United States Patent [19]
Tangney et al.

[11] Patent Number: 5,843,720
[45] Date of Patent: Dec. 1, 1998

[54] INTRODUCTION OF DNA INTO BACILLUS STRAINS BY CONJUGATION

[75] Inventors: Martin Tangney, Edinburgh, Scotland; Christian Hansen, Bagsvaerd, Denmark; Poul Erik Pedersen, Bagsvaerd, Denmark; Per Lina Jorgensen, Bagsvaerd, Denmark; Steen Troels Jorgensen, Bagsvaerd, Denmark

[73] Assignee: Novo Nordisk A/S, Bagsvaerd, Denmark

[21] Appl. No.: 925,927

[22] Filed: Sep. 8, 1997

Related U.S. Application Data

[63] Continuation of PCT/DK96/00112 Mar. 22, 1996.

[30] Foreign Application Priority Data

Mar. 22, 1995 [DK] Denmark ................................. 0294/95
Jul. 6, 1995 [DK] Denmark ................................. 0798/95

[51] Int. Cl.⁶ ............................. C12P 21/01; C15N 1/21; C15N 15/64; C15N 15/75
[52] U.S. Cl. ................ 435/69.1; 435/172.1; 435/252.31; 435/320.1
[58] Field of Search ............................. 435/69.1, 172.1, 435/172.3, 320.1, 183, 252.31; 536/23.1, 23.2, 24.1

[56] References Cited

U.S. PATENT DOCUMENTS 5,346,818 9/1994 Schäfer et al. ........................ 435/172.3

FOREIGN PATENT DOCUMENTS 0 582 541 A2 2/1994 European Pat. Off. .
WO 91/09129 6/1991 WIPO .
WO 94/14968 7/1994 WIPO .

OTHER PUBLICATIONS

Selinger et al., "Mobilization of Closely Related Plasmids pUB110 And pBC16 by Bacillus Plasmid pX0503 Requires Trans–Acting Open Reading Frame β", Journal of Bacteriology, Jun. 1990, vol. 172. No. 6, pp. 3290–3297.

*Primary Examiner*—Nancy Degen
*Attorney, Agent, or Firm*—Steve T. Zelson; Elias J. Lambiris

[57] ABSTRACT

The present invention relates to methods of constructing recombinant Bacillus strains encoding a polypeptide of interest, in which method a DNA construct comprising a DNA sequence encoding the polypeptide of interest is introduced into a recipient Bacillus cell by conjugation from a donor cell.

13 Claims, No Drawings

16 # INTRODUCTION OF DNA INTO BACILLUS STRAINS BY CONJUGATION

CROSS-REFERENCE TO RELATED APPLICATIONS

This application is a continuation of PCT/DK96/00112 filed Mar. 22, 1996 which claims priority under 35 U.S.C. 119 of Danish applications 0294/95 and 0798/95 filed Mar. 22, 1995 and Jul. 6, 1995, respectively, the contents of which are fully incorporated herein by reference.

FIELD OF THE INVENTION

The present invention is in the field of introduction of DNA into cells of Bacillus spp. and of the production of polypeptides by cultivation of such cells.

BACKGROUND OF THE INVENTION

Traditionally, three different methods have been used for introducing DNA into strains of Bacillus sp. The first method, which is generally useful only for cells of *B. subtilis* 168, is transformation of competent cells, the second is based on the principles of electroporation, and the third is based on transformation of protoplasts.

Especially the protoplast transformation and the transformation of competent cells are widely used. However, while protoplast transformation functions for a number of different Bacillus sp. it cannot, in general, be accomplished in less than two weeks which makes this method cubersome to use. Furthermore, as mentioned above, transformation of competent cells has generally only been shown to work satisfactory for cells of *B. subtilis* 168.

It has been shown that some strains of Bacillus may take up DNA by means of conjugation, i.e. by exchange of genetic material mediated by certain "transfer plasmids".

More specifically, Koehler and Thorne (in Journal of Bacteriology, November 1987, pp. 5771–5278) describe a 55 kb plasmid, pLS20, which is capable of mediating transfer of plasmids between Bacillus sp. The transfer of the tetracycline resistance plasmid pBC16 and the *Staphylococcus aureus* kanamycin resistance plasmid pUB110, respectively, were shown to be mediated by the plasmid pLS20 from a strain of *B. subtilis* (natto) to strains of the Bacillus spp. *B. anthracis, B. cereus, B. licheniformis, B. megaterium, B. pumilus, B. subtilis* and *B. thuringiensis*. Other plasmids were found to be unable to transfer by use of pLS20. The transfer of plasmids mediated by pLS20 was concluded to take place by donation rather than conduction, i.e. without physical association of the two plasmids.

In Journal of Bacteriology, June 1990, pp. 3290–3297 Selinger et al. identify an open reading frame β (ORF-β) region in the nonconjugative plasmids pUB110 and pBC16 and conclude that this region is essential for mobilization of the plasmids by the conjugational plasmid pLS20 or its derivatives. Also another region of pUB110 and pBC16 located 5' to ORF-β (and presumably including oriT) is shown to be necessary for mobilization. ORF-β is acting in trans whereas the other region is cis-acting.

It is an object of the present invention to provide improved systems for introducing DNA into strains of Bacillus sp. and to use these systems for the production of polypeptides of interest.

BRIEF DISCLOSURE OF THE INVENTION

It has surprisingly been found that conjugation may be used for introducing DNA encoding a translocated polypeptide into a number of different Bacillus sp., in particular industrial Bacillus strains, and further that the use of conjugation for this purpose is much more simple, efficient and fast than the above mentioned conventionally used methods. In addition the transfer frequency is much higher than that observed for conventionally used methods. Furthermore, conjugation may be used to introduce DNA into cells for which conventional methods have proved unsatisfactory or simply not working.

Accordingly, in a first aspect the invention relates to a method of producing a translocated polypeptide comprising cultivating a cell of Bacillus which through conjugation has aquired a DNA construct encoding said translocated polypeptide.

In further aspects the invention relates to methods of introducing a DNA construct encoding a polypeptide of interest into recipient cells of Bacillus sp. by conjugation, in which methods a population of bacterial donor cells harboring i) a plasmid comprising the DNA construct and at least one cis-acting DNA sequence required for the transfer of said plasmid by conjugation in the presence of a trans-acting mobilizing element, and ii) at least one DNA sequence encoding said trans-acting mobilizing element, and a population of Bacillus sp. recipient cells are mixed under conditions allowing the plasmid to be transferred from the population of donor cells to the population of recipient cells by conjugation. The recipient cells may e.g. be cells of industrial Bacillus strains or alkalophilic Bacillus sp. for which known DNA introduction methods either are non-existing or very laborious.

DEFINITIONS

The term "translocated polypeptide" is intended to indicate that the polypeptide to be expressed carries a signal sequence which enables it to be translocated across the cell membrane. In particular, the translocated polypeptide may be a secreted polypeptide or a polypeptide involved in the secretory machinery of the Bacillus cell in question.

In the present context the term "cis-acting DNA sequence required for the transfer of said plasmid by conjugation in the presence of a trans-acting mobilizing element" is intended to indicate a DNA sequence or DNA site necessary for mobilization to take place, which must be located on the plasmid which is to be introduced into the recipient cell. The cis-acting DNA sequence may be oriT or a functional analogue or part thereof.

The term "trans-acting mobilizing element" is intended to indicate a protein mediating conjugative transfer of DNA sequences containing the cis-acting DNA sequence defined above. The trans-acting mobilizing element may be a protein encoded by a conjugational plasmid, such as pLS20, or a part or derivative thereof, or may be a protein encoded by a DNA sequence such as orf-β or a functional analogue or part thereof. It will be understood that since the mobilizing element is acting in trans it may be encoded by DNA present in the genome of the donor cell or on a second plasmid, such as a conjugative plasmid, present in said donor cell.

DNA sequences comprising oriT and orf-β, respectively, are described by Sellinger et al., op. cit.

The terms "functional analogue" or functional part" as used about oriT and orf-β, respectively, are intended to indicate that a modified gene sequence may be used as long as the plasmid mobilizing function conferred by the modified gene sequence is not substantially impaired. For instance, it is contemplated that parts or subsequences of oriT and orf-β (as described by Sellinger et al.), respectively, may exert the desired function. Functional parts or analogues of oriT and orf-β respectively, may be identified by modifications of the native oriT or orf-β, such as by deletion, insertion or substitution of one or more nucleotides by conventional DNA modification techniques and subsequent testing for plasmid mobilization capability of the resulting part or analogue.

The term "conjugative plasmid" is intended to cover any plasmid which is able to mediate transfer of DNA by conjugation. One very suitable example is the plasmid pLS20 (described by Sellinger et al., op. cit.) or a plasmid essentially identical thereto, or a derivative of pLS20 having retained the plasmid mobilizing capability of pLS20. The term "derivative" as used in connection with the plasmid pLS20 is intended to indicate a genetically modified plasmid, typically reduced in size, which has retained the conjugation mediating capability of said plasmid.

The term "curable plasmid" is intended to indicate that a cell harboring the plasmid may be cured from said plasmid by an externally applied factor. For instance, the plasmid may carry a conditional origin of replication allowing the plasmid to replicate under certain (permissive) conditions and unable to replicate under other (non-permissive) conditions. The plasmid may, for instance, be one which is temperature-sensitive for replication.

It should be noted that, in the present context, the term "plasmid" is also intended to denote a bacteriophage or other DNA molecule capable of functioning as an autonomously replicating extrachromosomal element.

DETAILED DISCLOSURE OF THE INVENTION

Production of a Translocated Polypeptide

In the method according to the first aspect of the invention a translocated polypeptide is produced by cultivation of a cell of Bacillus which through conjugation has aquired a DNA construct encoding the translocated polypeptide in question.

The conjugation is preferably accomplished by use of a plasmid carrying the DNA construct and at least one cis-acting sequence required for transfer of said plasmid by conjugation in the presence of at least one mobilizing element, the mobilizing element being provided in trans, i.e. by any of the methods of conjugation which are described in much further detail in the following disclosure.

One type of Bacillus strain of particular interest in connection with the present invention is a cell of an alkalophilic Bacillus. Examples of alkalophilic Bacillus sp. include those described in U.S. Pat. No. 5,217,878, e.g. Bacillus sp. PB92, U.S. Pat. No. 3,723,250 and U.S. Pat. No. 3,840,433.

Another type of Bacillus strain of interest for the present method is a cell of an industrial Bacillus. The term "industrial Bacillus strain" is intended to indicate a non-recombinant strain of a Bacillus sp., different from *Bacillus subtilis* 168, which is capable of producing more than 5 g/l of a secreted polypeptide. Of particular interest is an industrial Bacillus strain which is a mutant of a naturally occurring strain which has been mutated to and selected on the basis of its capability of producing translocated polypeptides in a high yield, i.e. a yield which is higher than that obtainable from the naturally occurring parent strain. The mutant strain may be produced by any type of mutation such as classical mutation involving subjecting cells of the strain to be mutated to a physical or chemical mutagenizing agent such as ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used the mutagenesis is typically performed by incubating the cell to be mutagenized in the presence of the mutagenizing agent of choice under suitable conditions for the mutagenesis to take place, and selecting for mutated cells which are capable of producing and excreting high amounts of translocated polypeptides, including high amounts of the translocated polypeptide in question. Such mutant may be referred to as a "high-yielding mutant" in the following disclosure.

Examples of industrial Bacillus strains are specified in EP 134 048 and include strains of *B. licheniformis*, *B. amyloliquefaciens* and *B. lentus*.

Further examples of suitable cells of Bacillus (which may or may not be industrial and/or alkalophilic) may be selected from the group consisting of *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium*, and *Bacillus thuringiensis*.

In a preferred embodiment of this aspect of the invention the Bacillus cell is free from undesired selectable marker gene(s) such as a gene encoding an antibiotic resistance marker which has been used for selection of cells having received the DNA sequence encoding the translocated polypeptide. Methods of obtaining Bacillus cells free from undesired selectable marker gene(s) are described further below.

In a further preferred embodiment the Bacillus cell is free from any conjugative elements which have been used for the construction of the cell by conjugation. Methods of obtaining such cells are described further below.

In order improve the stability of the Bacillus cell to be used in the method according to this aspect of the invention it is desirable that the DNA construct encoding the translocated polypeptide is integrated into the genome of the Bacillus cell. This may be accomplished when the plasmid carries one or more DNA sequences which are sufficiently homologous to a part of the genome of the recipient cell to allow for homologous recombination. Suitable methods for obtaining stable integration of the DNA construct in the genome of the reciepient cell are discussed in further details below.

The translocatable polypeptide to be produced in accordance with the method of the first aspect of the invention is preferably a secreted polypeptide or a polypeptide of the secretory pathway of a secreting cell.

The secreted polypeptide may be an enzyme, e.g., selected from an amylolytic enzyme, a lipolytic enzyme, a proteolytic enzyme, a cellulytic enzyme, an oxidoreductase or a plant cell-wall degrading enzyme. Examples of such enzymes include AMG, amylase, lipase, cutinase, esterase, cellulase, hemicellulase, xylanase, protease, peroxidase, laccase, phenol oxidase, catalase, glucose oxidase, oxidase, phytase, lyase, pectinase, glucosidase, mannosidase, isomerase, invertase, transferase, ribonuclease, galactosidase and chitinase. Alternatively, the secreted polypeptide may be a hormone, a growth factor, a receptor or the like.

A preferred example of a polypeptide of the secretory pathway is PrsA (WO 94/19471, the content of which is incorporated herein by reference).

When the translocated polypeptide is a secreted protein the method of this first aspect of the invention preferably further comprises a polypeptide recovery step. The polypeptide may be recovered by conventional procedures including separating the cells from the medium by centrifugation or filtration, if necessary after disruption of the cells, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

Methods of the Invention for DNA Introduction by Conjugation

Using an Industrial Bacillus or an Alkalophilic Bacillus Recipient Cell

The second main aspect of the invention relates to a method of introducing a DNA construct encoding a polypeptide of interest into a cell of a Bacillus sp., in which method a population of bacterial donor cells harboring i) a plasmid comprising the DNA construct and at least one cis-acting DNA sequence required for the transfer of said plasmid by conjugation in the presence of a trans-acting mobilizing element, and ii) at least one DNA sequence encoding said trans-acting mobilizing element, and a population of Bacillus sp. recipient cells are mixed under conditions allowing the plasmid to be transferred from the population of donor cells to the population of recipient cells by conjugation, the Bacillus sp. being an alkalophilic Bacillus sp. and/or an industrial Bacillus sp.

This aspect of the invention is particularly advantageous since strains of alkalophilic Bacillus sp. and/or industrial Bacillus strain—in general—have been found to be non-transformable by competence and thus only subject to protoplast transformation which—as described above—is a very cumbersome method for introduction of DNA.

Examples of alkalophilic Bacillus sp. and industrial Bacillus strains are given above. In particular, the Bacillus cell to be used in accordance with this aspect of the invention may be a high-yielding mutant.

Using an Auxotrophic Donor Cell

The third aspect of the present invention relates to a method of constructing a cell of a Bacillus sp. harboring a DNA construct encoding a polypeptide of interest, in which method a population of auxotrophic bacterial donor cells harboring i) a plasmid comprising the DNA construct and at least one cis-acting DNA sequence required for the transfer of said plasmid by conjugation in the presence of a trans-acting mobilizing element, and ii) at least one DNA sequence encoding said trans-acting mobilizing element, and a population of unmarked Bacillus sp. recipient cells are mixed under conditions allowing the plasmid to be transferred from the population of the auxotrophic donor cells to the population of unmarked recipient cells by conjugation, and the auxotrophic property of the donor cell is exploited to select for recipient cells.

This aspect of the invention is clearly advantageous in that no selection need to be made for recipient cells—they are the only one remaining when exploiting the auxotrophic property of the donor cell.

The donor cell may, e.g., be auxotrophic for specific amino acids. A particular preferred donor to be used in a method of the present invention is a donor which is auxotrohic for D-alanine, i.e. a donor which is dal⁻. After the conjugation treatment has been accomplished the mixture of dal⁻ donor cells and recipient cells is cultivated on or in a medium devoid of D-alanine, i.e. as medium in or on which the dal⁻ donor cells are unable to grow. Thereby only recipient cells remain. The principle of using an auxotrophic marker is described in, e.g., U.S. Pat. No. 4,920,048.

Subsequently, only selection for recipient cells having aquired the DNA construct of interest must be made, conveniently by use of a selection marker, e.g. an antibiotic resistance, encoded by the plasmid.

Using a Curable Plasmid

In a fourth aspect the invention relates to a method of introducing a DNA construct encoding a polypeptide of interest into a cell of a Bacillus sp., in which method a population of bacterial donor cells harboring i) a curable plasmid comprising the DNA construct and at least one cis-acting DNA sequence required for the transfer of said plasmid by conjugation in the presence of a trans-acting mobilizing element, and ii) at least one DNA sequence encoding said trans-acting mobilizing element, and a population of Bacillus sp. recipient cells are mixed under conditions allowing the plasmid to be transferred from the population of donor cells to the population of recipient cells by conjugation.

To the best of the present inventors's knowledge the present invention constitutes the first disclosure of the use of elements from mobilizable plasmids to confer on previously non-mobilizable, curable, in particular temperature-sensitive, plasmids the ability to be transferred between strains by conjugation.

The use of a curable plasmid is of particular relevance for the construction of recipient cells having received some elements of the plasmid which through conjugation has been transferred into the cell, but which is free from other elements such as the cis-acting DNA sequence required for the transfer of the plasmid by conjugation. In such cases it may be advantageous to integrate the DNA construct encoding a polypeptide of interest into the genome of the recipient cell, optionally together with other elements to be retained in the cell, whereas the elements which are not desired in the cell (such as the cis-acting DNA sequence) are retained on the plasmid. After genomic integration has taken place the cell is cured from the curable plasmid carrying the unwanted elements. Methods of achieving genomic integration is described further below.

The curable plasmid to be used in the method according to this aspect of the invention may be constructed by combining the respective elements (e.g. a temperature sensitive origin of replication, a cis-acting DNA sequence, a DNA construct of interest, a selectable marker gene, etc.) in accordance with methods known in the art, typically by modification of either a curable plasmid or a plasmid carrying the cis-acting DNA sequence.

Genomic Integration of a DNA Construct of Interest

In a further aspect the invention relates to a method of introducing a DNA construct encoding a polypeptide of interest into a cell of a Bacillus sp. and obtaining stable integration thereof into the genome of the recipient cell, in which method a population of bacterial donor cells harboring i) a plasmid comprising the DNA construct, at least one cis-acting DNA sequence required for the transfer of said plasmid by conjugation in the presence of a trans-acting mobilizing element, and a first origin of replication and a second origin of replication in the same orientation as the first origin of replication, which first and second origins of replication are sufficiently similar to be functional with the same replication factor(s), the first and second origins of replication dividing the plasmid into two parts, a first part (a) comprising the first origin of replication, one or more functional genes encoding the replication factor(s) required for plasmid replication from said first and second origin of replication, and the cis-acting DNA sequence(s) required for the transfer of the plasmid by conjugation in the presence of a trans-acting mobilizing element, and a second part (b) comprising the second origin of replication, the DNA construct encoding a polypeptide of interest, and a DNA sequence which is homologous with a region of the genome of the recipient cell, and ii) at least one DNA sequence encoding said trans-acting mobilizing element, and a population of Bacillus sp. recipient cells are mixed under conditions allowing the plasmid to be transferred from the population of donor cells to the population of recipient cells by conjugation and allowing the DNA construct to be integrated into the genome of the cell without the concomitant integration of the cis-acting DNA sequence.

The second origin of replication may be derived from the same plasmid as the first origin of replication. It is preferred that a gene encoding the replication factor associated with the second origin of replication has been deleted or modified.

When introduced into the recipient cell replication of the plasmid gives rise to the formation of two different progeny vectors. The first progeny vector comprises (i) a first origin of replication; (ii) one or more genes encoding the replication factor(s) required for replication from said origin. The second progeny vector comprises (iii) a second origin of replication; (iv) the DNA sequence of interest, and a DNA sequence which is homologous with a region of the genome of the recipient cell, said second progeny vector lacking a functional gene coding for a replication factor required for replication from the second origin of replication carried on said second progeny vector.

When the second origin is located in the same orientation on the parent plasmid as the first origin, the various DNA sequences intended to be integrated into the recipient genome and located downstream of the second origin, but upstream of the first origin (i.e. the DNA sequence of interest, and the DNA sequence which is homologous with a region of the cell genome) will be present on the second progeny vector following plasmid replication. Continued culturing of the recipient cells may spontaneously result in the integration of said second progeny vector into the bacterial genome by homologous recombination and loss of the first progeny vector from the cells with a certain frequency. Thus, when the cis-acting element is located in the first part of the plasmid, i.e. between the first and second origin of replication, it is avoided that this sequence be integrated in the genome together with the DNA sequence of interest. The integration method according to this aspect is described to a further extent in WO 91/09129.

Amplification of Genomic DNA Sequences

In a still further aspect the invention relates to a method for in vivo amplification of a DNA sequence B present in the genome of a recipient Bacillus sp. cell, in which method a) a population of bacterial donor cells harboring i) a plasmid comprising at least one cis-acting DNA sequence required for the transfer of said plasmid by conjugation in the presence of a trans-acting mobilizing element, and the following structure:

C-M-A-D, in which

A denotes a DNA sequence which is homologous with a genomic DNA fragment either flanking or overlapping the DNA sequence B to be amplified or being a subsequence of the DNA sequence B constituting one of the ends of said sequence B, C denotes a DNA sequence which is homologous with a genomic DNA fragment either flanking or overlapping the DNA sequence B to be amplified or being a subsequence of the DNA sequence B constituting one of the ends of said sequence B, the sequence C being located in the opposite end of the sequence B as compared to A, D denotes a DNA sequence which is homologous with a genomic DNA fragment located distal for C as compared to B, and M denotes a DNA sequence encoding a selection marker, and ii) at least one DNA sequence encoding said transacting mobilizing element, and a population of recipient Bacillus sp. cells, which in their genome harbors at least one copy of the DNA sequence B to be amplified, are mixed under conditions allowing the plasmid to be transferred from the population of donor cells to the population of recipient cells by conjugation, b) recipient cells are selected in which the DNA sequence M has been integrated in the genome either upstream or downstream of the DNA sequence B together with the sequence A, which cells comprise, in any orientation, the structure A-B-C-M-A-D, and c) the cells selected in step b) are propagated under increasing selection pressure for the selection marker encoding by the DNA sequence M so as to obtain a cell which has obtained an increased number of genomically integrated copies of the DNA sequences B and M as compared to the parent cell.

The plasmid is transferred into the recipient cell by conjugation mediated by a conjugative plasmid, after which cells are selected (step b)) in which the DNA sequence M has been integrated in the genome either upstream or downstream of the DNA sequence B together with the sequence A, which cells comprise, in any orientation, the structure A-B-C-M-A-D.

The cells selected in step b) are propagated under increasing selection pressure for the selection marker encoding by the DNA sequence M so as to obtain a cell which has obtained an increased number of genomically integrated copies of the DNA sequences B and M as compared to the parent cell.

By use of this method for amplification of a genomic DNA sequence integration of the cis-acting and trans-acting conjugative elements may be avoided.

Preferred Embodiments of the Methods of the Invention

In the following preferred embodiments of the above described methods of the invention are described. It is to be understood that the subject-matter of these embodiments of the invention are generally applicable for the method according to each and any of the main aspects dealt with above except if otherwise stated.

The Recipient Cell

It is preferred that the recipient cell to be used in any of the conjugation methods of the invention is a cell of an alkalophilic Bacillus sp. or a cell of an industrial Bacillus strain. The recipient cell may further be a cell of a Bacillus sp., such as *Bacillus subtilis, Bacillus licheniformis, Bacillus lentus, Bacillus brevis, Bacillus stearothermophilus, Bacil-*

*lus alkalophilus, Bacillus amyloliquefaciens, Bacillus coagulans, Bacillus circulans, Bacillus lautus, Bacillus megaterium* or *Bacillus thuringiensis*. The latter species may belong to the group of industrial Bacillus strains or alkalophilic Bacillus sp. In particular, it is preferred that the recipient cell is a mutant cell capable of producing a heterologous polypeptide, in particular a translocated polypeptide in high yields, i.e. yields which are higher than those obtainable by the unmutated parent cell.

If the cis-acting and/or transacting conjugative element(s) and/or any undesired selectable marker gene(s) (which may have been used in the construction of the cell) have been integrated in the genome of the recipient cell when using a conjugation method of the invention it may be desirable to delete these elements, in particular from a product approval point of you. Accordingly, in as further embodiment the invention provides for a deletion or inactivation of cis-acting and/or trans-acting elements (e.g. oriT and/or orf-β or functional parts or analogues thereof) and/or undesired selectable marker gene(s) from the genome of the recipient cell. This may be accomplished by methods known in the art for inactivation or deletion of genes such as gene disruption or gene replacement or by locating the DNA fragments being or encoding these elements inbetween homologous sequences which may recombine and thereby excise the intervening undesired DNA fragment. Alternatively, the undesired element(s) may be removed by the use of a resolvase system in which the element in question is located between resolvase target sequences which upon action of a resolvase protein is recombined whereby the intervening DNA fragment is excised. The use of a resolvase or a homologous recombination system for excision of undesired DNA sequences is described in detail in PCT/DK96/00038.

The Donor Cell

The bacterial donor cell to be used in any of the methods of the present invention may be a cell of an Eschericia sp., such as *E. coli*, but is more preferably a cell of a Bacillus sp., such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium* or *Bacillus thuringiensis*.

In addition or alternatively, the donor cell may be auxotrophic, e.g. as described in further detail above in the section entitled "Methods of the invention for DNA introduction by conjugation—using an auxotrophic donor cell".

The donor cell may harbor, in its genome, one or more DNA sequences encoding the trans-acting element required for conjugation to take place.

Transacting Element

It will be understood that in order to function properly in the methods of the present invention the transacting element, such as orf-β, should be operably linked to regulatory DNA sequences (such as a promoter, a terminator, a ribosome binding site, etc.) ensuring that the gene be transcribed and translated. For instance, the gene should be preceeded by a suitable promoter, e.g. the one, which in nature is found to be associated with the gene, but more preferably a promoter ensuring a strong transcription from the gene. Furthermore, it may be advantageous to insert an extra promoter in front of the orf-β sequence and/or insert two or more copies of the orf-β sequence, optionally each preceeding by a strong promoter. For instance, the insertion of the *B. amyloliquefaciens* α-amylase promoter in front of the orf-β and its natural promoter was found to result in a significantly improved transfer frequency. Examples of other strong promoters which may be inserted as extra or alternative promoters include the promoters of the *Bacillus licheniformis* α-amylase gene (amyL), the promoters of the *Bacillus stearothermophilus* maltogenic amylase gene (amyM), etc.

Curable Plasmid

In a highly preferred embodiment the DNA construct to be introduced into the recipient cell is present on a curable plasmid which also comprises the cis-acting sequence is a curable plasmid. The curable plasmid and its use is further described above in the section entitled "Methods of the invention for DNA introduction by conjugation—using a curable plasmid".

Genomic Integration of the DNA Construct of Interest

Although the DNA construct encoding the polypeptide of interest, which is to be introduced in a recipient cell in accordance with any of the above described generel aspects of the invention, may exist as an extrachromosomal element in the recipient cell (e.g. carried on the plasmid used for the introducing the DNA into the cell) it is generally preferred that the DNA construct be integrated in the genome of the recipient cell, since genomically integrated DNA is generally considered more stable.

The genomic integration may be achieved by well-known methods conveniently based on recombination between homologous sequences on the plasmid and the genome, respectively. In one embodiment genomic integration may be achieved when the plasmid to be transferred is a plasmid which comprises the following structure:

cis-R(1)-DNA-R(2)

in which
  cis denotes the cis-acting DNA sequence required for conjugational transfer,
  DNA is the DNA construct to be introduced into the recipient cell, and
  R(1) and R(2), respectively, are a DNA sequence sufficiently homologous to a part of the recipient cell genome to allow for integration of the DNA construct located between R(1) and R(2) into the genome of the recipient cell by double crossing over.

The plasmid may conveniently be a curable plasmid, e.g. one which comprises a temperature sensitive origin of replication located on either side of the fragment comprising R(1)-DNA-R(2). The use of a curable plasmid has the additional advantage that it is possible to remove the cis-acting DNA sequence required for conjugation to take place from the cell once conjugation has taken place.

When a curable plasmid is used it is desirable that the method comprises the further step of selecting for recipient cells having integrated the DNA construct encoding a polypeptide of interest into the genome and from which the plasmid carrying the cis-acting element has been lost.

Another very convenient method of obtaining stable integration is based on the use of the "one-plasmid system" further described in WO 91/09129. The methods of the present invention may conveniently be carried out by use of such system.

In connection with the embodiments of the present invention which relate to genomic integration by use of homologous regions, the term "homologous" region of the genome is preferably a region which is unessential for survival and proper functioning of the recipient cell.

Still another suitable method for achieving genomic integration is by use of a transposition system, e.g. a system as described in PCT/DK96/00038 in which the DNA construct to be integrated is located in between transposase target sequences.

Furthermore, as indicated above in order to improve the efficiency of the integration according to any of the above described methods one may utilise a curable plasmid. The plasmid may, for instance, be one which is temperature-sensitive for replication. Another way of increasing the efficiency of integration and subsequent loss of the first progeny vector from the cells may be to treat the cells transformed with the plasmid with a plasmid-curing agent, e.g. novobiocin (Gadó, I. et al., 1987. Zbl. Bakt. Hyg. A. 265, 136–145), after culturing the host cells under selective conditions as described above.

Amplification of the DNA Sequence Encoding a Polypeptide of Interest

The conjugation method of the invention may advantageously be used to achieve amplification of genomic DNA sequences present in the genome of the recipient cell. A very convenient method for achieiving amplification of genomic DNA sequences is described in WO 94/14968, the contents of which are incorporated herein by reference. The genomic DNA sequence to be amplified may be the one encoding a polypeptide of interest, which has been introduced into the recipient cell by a conjugation method of the invention.

A Recipient Cell of the Invention

In a still further aspect the invention relates to a cell of a Bacillus sp. produced by a conjugation method of the invention which harbors a DNA construct of interest and a cis-acting DNA sequence required for the conjugation to take place. The cell is preferable of a cell of any of the Bacillus sp. specified above in the section entitled "Recipient cells" and most preferably a high-yielding mutant.

A Method of Producing a Polypeptide

In a still further aspect the invention relates to a method of producing a polypeptide of interest, which method comprises cultivation of a cell produced by a method of the present invention as defined above under conditions conducive for the production of the polypeptide of interest, and optional recovery of the polypeptide of interest.

The polypeptide may be recovered by conventional recovery or purification techniques, examples of which are mentioned further above.

The method in accordance with this aspect of the invention is particularly preferred for the production of translocated polypeptides, such as a secreted polypeptide or a polypeptide functioning in the secretory pathway of the recipient cell. Preferred examples of secreted polypeptides, such as enzymes, are mentioned above.

Plasmids and Construction of DNA Constructs

In a final aspect the invention relates to a non-naturally occuring plasmid which comprises oriT or a functional part or analogue thereof. The plasmid may further comprise a DNA sequence conferring temperature sensitivity to the plasmid and/or a DNA construct encoding a polypeptide of interest, in particular a translocated polypeptide as defined above.

The DNA constructs and plasmids to be used in a method of the invention may be synthesized through a series of genetic manipulations employing methods and enzymes known in the art.

MATERIALS AND METHODS

Bacterial strains and plasmids
Donor strains:
B. subtilis

| | |
|---|---|
| DN1280 | dal (ref. 2) |
| PP289-5 | DN1280 (pLS20; tra$^+$), (pBC16; Tc$^r$) |
| MT101 | DN1280 (pX0503; tra$^+$MLS$^r$) |
| MT107 | DN1280 (pX0503; tra$^+$MLS$^r$) (pUB110; Km$^r$) |

Recipient strains:

| | |
|---|---|
| B. subtilis W23 | BGSC |
| B. lentus C360 | (ref. 3) |
| B. licheniformis ATCC 102 | |

Plasmids:

| | | |
|---|---|---|
| pUB110 | Mob$^+$Kin$^r$ | BGSC |
| pBC16 | Mob$^+$Tc$^r$ | (ref. 4) |
| pLS20 | Tra$^+$ | (ref. 1) |
| pX0503 | Tra$^+$MLS$^r$ (pLS20::Tn917, 60 kb) | (ref. 1) |

Media and growth conditions. The conjugation methods is a modified version of the methods described by Koehler and Thorne (ref. 1). All bacterial strains were routinely grown on LB agar plates (Maniatis,T et al. 1982, ref. 5), supplemented as appropriate with D-alanine (50 µg/l) and antibiotics. (For better growth of the alkalophile strains the LB media could be buffered with 50 mM NaHCO$_3$). Freshly made over night cultures were used for conjugation.

Matings. Overnight cultures (14–24 hr) of donor and recipient strains were transferred to LB+D-alanine plates, and an inoculum containing 5–10 colonies of each strain were mixed. After mixing the strains, the cells were spread over the hole plate. The matings were incubated for at least 4 hr at 30°–37° C. The mating plates were either replicated to selective plates (=LB agar with the appropriate antibiotics but without D-alanine) or the cells were resuspended in LB media and spread in dilutions up to 10$^5$ on selective plates. From these plates conjugants were scored after 1 to 2 days at 30°–37° C. and further purified on selective plates.

ref. 1 Koehler, T. M., Thorne, C. B., 1987, J. Bact vol 169, 11 p. 5271–5278 ref. 2 Diderichsen, B., 1986. In Bacillus Molecular genetics and biotechnology applications. p. 35–46.

ref. 3 Aunstrup, K., H. Outtrup, O. Andresen and C. Dampmann. 1972. Proteases from alkalophilic Bacillus species, p. 299–305. In Proceedings of the forth international symposium on fermentation technology. Society of fermentations technology, Osaka, Japan.

ref. 4 Bernhard, K., H. Schrempf and W. Goebel. 1978. Bacteriocin and antibiotic resistance plasmids in B. cereus and B. subtilis. J. Bacteriol. 133: p. 897–903.

ref. 5 Maniatis,T et all 1982. Molecular cloning: A laboratory manual. Cold Spring Harbor Laboratory, Cold Spring Harbor, N.Y.). The mating plates were either replicated to selective plates (=LB agar with the appropriate antibiotics but without D-alanine) or the cells were resuspended in LB media and spread in dilutions up to 10$^5$ on selective plates. From these plates conjugants were scored after 1 to 2 days at 30°–37° C. and further purified on selective plates.

EXAMPLE 1

A) Construction of a Temperature-sensitive Transposon-delivery Vector Encoding Savinase®

Savinase® is the extracellular, alkaline protease from Bacillus lentus. A vector expressing Savinase® and useful for the delivery of this gene by transposition is pMOL553. This plasmid was constructed in two steps.

Step 1

A BamHI site was introduced into the transposon of pHV1248 (Petit, M.-A., Bruand, C., Janniere, L. Ehrlich, S. D. (1990) Tn10-derived transposons active in *Bacillus subtilis, J. Bacteriol.,* 172:6736–6740) immediately upstream of the cat gene. The BamHI site was inserted by use of the PCR based SOE technique described earlier (Horton, R. M. et al. (1989) Gene, pp. 61–68). Two seperate PCR reactions were performed using the pHV1248 plasmid as template. The oligoes for the first PCR reaction were primer 1: CCCACT<u>GGATCC</u>AATTTTCGTTTGTTG (SEQ ID NO: 1) and primer 2: GCAAATTGATCCAAGAGAAC-CAAC (SEQ ID NO:2). The underlined bases in primer 1 show the position of the BamHI site. The second PCR reaction was based on primer 3: CAACAAACGAAAAT-TGGATCCAGTGGG (SEQ ID NO:3) and primer 4: GCA-CATCATCATCATAAGC (SEQ ID NO:4). Both PCR reactions were performed by standard procedures using temperatures of 96° C. at denaturation, 55° C. at annealing and 72° C. at the extension step. A total of 20 cycles were performed. Both fragments were purified from an agarose gel and 500 ng of each were used for a second 5 cycle PCR reaction: 96° C. for 2 min., 50° C. for 5 min and 72° C. for 1 min. Primer 2 and primer 4 (100 pmol) were added at 96° C. and a third 25 cycle PCR reaction was initiated: 96° C. for 30 sec., 55° C. for 30 sec. and 72° C. for 90 sec. The final PCR fragment of 1330 bp was digested with HindIII and cloned back into the HindIII digested pHV1248 giving the plasmid pMOL610. The ligation mixture was transformed into *E. coli* SJ2 (Diderichsen et al., 1990, J. Bacteriol. 172, 4315–4321). The position of the BamHI site in pMOL610 was verified by restriction digest.

Step 2

In this step the entire Savinase® gene was cloned into the BamHI site of pMOL610. The total Savinase® gene and promoter region was amplified from a pSX222 (WO 92/11357) plasmid by PCR using primers with BamHI restriction sites (underlined) 5: CCGGC<u>GGATCC</u>AAGGGGTGATCG (SEQ ID NO:5) and primer 6: GGGGTACTAGTAACCCGGGCCCGGCGTAGA<u>GGATCC</u>ATACACAAA (SEQ ID NO:6). The PCR reaction was performed as follows: 96° C. for 30 sec., 55° C. for 30 sec., and 72° C. for 120 sec. After 20 cycles the PCR fragment was BamHI digested, purified and cloned into the BamHI site of pMOL610. The cloning was verified by restriction digests and a distinct protease phenotype in *B. subtilis* (e.g. in strain DN1885, (Diderichsen et al., 1990, J. Bacteriol. 172, 4315–4321.), or protease-deficient derivatives of this strain).

The vector encoding Savinase® thus constructed is pMOL553. The full sequence of this plasmid is given in SEQ ID No 1 of PCT/DK96/00038, and a restriction map in FIG. 1 of said application.

B) Construction of a Mobilizable Transposon Delivery Vector Encoding Savinase®

Mobilization of plasmid pUB110 by pLS20 or its derivatives has been described and analyzed in some details (Koehler, T. M. and Thorne, C. B. (1987). *Bacillus subtilis* (natto) plasmid pLS20 mediates interspecies plasmid transfer. J. Bacteriol., 169, 5271–5278; Selinger, L. B., McGregor, N. F., Khachatourians, G. G. and Hynes, M. F. (1990). Mobilization of closely related plasmids pUB110 and pBC16 by Bacillus plasmid pXO503 requires transacting open reading frame β. J. Bacteriol., 172, 3290–3297). We have used elements from these plasmids to mobilize the Savinase®-expressing transposon delivery vector.

Mobilization of pUB110 is dependent on a cis acting region (oriT) located 5' to orfβ (Selinger et al.,1990). A 555 bp segment from pUB110, extending from pos. 1020 to pos. 1575 in the pUB110 sequence, was PCR amplified using primers LWN5232 and LWN5233.

LWN5232:

5'-GTCGGAGCTCATTATTAATCTGTTCAGCAATCGGGC-3' (SEQ ID NO:7)

LWN5233:

5'-GTCGGAGCTCTGCCTTTTAGTCCAGCTGATTTCAC-3' (SEQ ID NO:8)

The amplified fragment was digested with SacI and initially cloned into the SacI site of an *E. coli* plasmid (a pUC19 derivative). The fragment was subsequently excised again using SacI, and cloned into the unique SacI site in the previously described plasmid pMOL553. The ligation mixture was transformed into *E. coli* SJ2 selecting Amp resistance. The resulting plasmid is pMOL553-oriT.

C) Construction of a Conjugative Donor Strain Containing a Mobilizable Transposon Delivery Vector Encoding Savinase®

Plasmids pLS20 and pBC16 can be transferred by conjugation from *B. subtilis* strain PSL1 UM13 into various Bacillus recipient strains (Koehler and Thorne, 1987).

DN1280 is a derivative of *B. subtilis* 168, containing a deletion in the dal gene (Diderichsen, B. (1986). A genetic system for stabilization of cloned genes in *Bacillus subtilis*, pp. 35–46). In A. T. Ganesan and J. A. Hoch (eds.), Bacillus molecular genetics and biotechnology applications, Academic Press, Inc., New York). DN1280 was rendered competent and transformed with plasmid pHV1248, selecting erythromycin resistance (5 μg/ml) at 30° C. The resulting strain was used as recipient in conjugation with PSL1 UM13. Both strains were mixed on an LB plate supplemented with phosphate (0.01M $K_3PO_4$), glucose (0.4%), starch (0.5%) and D-alanine (100 μg/ml), and incubated for 5 hours at 30° C. The plate was then replicated onto an LB plate as above, but in addition containing erythromycin (5 μg/ml) and tetracycline (5 μg/ml).

Single colonies appearing on the replica plate was assayed for their ability to transfer pBC16 into *B. subtilis* DN1885. Conjugation was performed by mixing of the strains on LB plates as above and incubation for 5 hours at 30° C. Replication was to LB plates with tetracycline (5 μg/ml), but without D-alanine. The omission of D-alanine effectively counterselects the dal⁻ donor strain. A few of the colonies assayed were able to transfer the $Tet^R$ marker into DN1885. This indicates that these colonies harbor pLS20 in addition to pBC16. One such colony was propagated at 50° C. in liquid TY medium containing tetracycline (5 μg/ml) and D-alanine (100 μg/ml), subsequently plated on LB containing tetracycline (5 μg/ml) and D-alanine (100 μg/ml), and replica plated onto LB containing D-alanine (100 μg/ml) and erythromycin (5 μg/ml) or chloramphenicol (6 μg/ml), respectively. A tetracycline resistant, erythromycin and chloramphenicol sensitive isolate was kept as PP289-5. This strain, which is dal⁻ and contains pLS20 and pBC16, can serve as a conjugation donor strain that allows the transfer of plasmids containing the pUB110 oriT into various recipient strains.

Accordingly, PP289-5 was rendered competent and transformed with the oriT containing derivative of pMOL553, pMOL553-oriT. Plasmids were prepared from the pooled transformants of *E. coli* SJ2, and the plasmid mixtures transformed into PP289-5, selecting resistance to tetracycline (5 μg/ml), chloramphenicol (6 μg/ml) and erythromycin (5 μg/ml) on LB plates containing D-alanine (100 μg/ml). The transformants were again pooled, and the pool used to transfer pMOL553-oriT into DN1885 by conjugation, using the method described above. Finally, the identity of the plasmids in the transconjugants were verified by restriction mapping, and a correct plasmid was kept (pMOL553-oriT). pMOL553-oriT was retransformed into PP289-5 for further use.

D) Conjugative Transfer of an Alkaline Protease Gene into an Alkalophilic Bacillus Strain PP289-5 containing pMOL553-oriT was used as a conjugation donor strain to transfer a homologous apr gene, encoding Savinase®, isolated from *Bacillus lentus,* into the alkalophile *Bacillus lentus* strain C360 (Aunstrup, K., Outtrup, H., Andresen, O., Dampmann, C. (1972) Proteases from alkalophilic Bacillus species, pp. 299–305). In Proceedings of the fourth international symposium on fermentation technology, Society of fermentation technology, Osaka, Japan).

One day old cells of the donor strain PP289-5/pMOL553-oriT were harvested from an LB plate supplemented with 50 μg/ml D-alanine, 5 μg/ml erythromycin, and 5 μg/ml tetracyclin. The recipient strain (C360) was harvested (one day old cells) from a LB9 plate (LB9=LB plate buffered to pH9 by 0.05M $HNa_2CO_3/H_2NaCO_3$).

The recipient and the donor strains were mixed on LB plates supplemented with 50 μg/ml D-alanine, and incubated for 5 hours at 30° C. The plate was then replicated onto an LB9 plate supplemented with 5 μg/ml erythromycin. Single colonies appearing on the replica plate (after 2 days at 30° C.) were reisolated on an LB9 plate supplemented with 5 μg/ml erythromycin. (By omitting the D-alanine in the selective plates the dal⁻ donor strain is killed and only the *B. lentus* recipient containing the mobilizable pMOL553-oriT plasmid will survive). The plasmids in several transconjugants of *B. lentus* were isolated and a restriction mapping confirmed the transfer of the pMOL553-oriT plasmid into *B. lentus.*

---

We claim:

1. A method of producing a translocated polypeptide comprising:

a) transferring a DNA construct encoding a translocated polypeptide to a Bacillus cell via conjugation; and b) cultivating the Bacillus cell in a medium under conditions so that the polypeptide is produced.

2. The method according to claim 1 wherein the DNA construct is a plasmid and comprises at least one cis-acting sequence required for transfer of said plasmid by conjugation in the presence of at least one mobilizing element, the mobilizing element being provided in trans.

3. The method of claim 1, wherein the cell of Bacillus is free from any mobilizing elements and/or selectable marker genes.

4. The method of claim 1, wherein the cell of Bacillus is selected from the group consisting of alkalophilic Bacilli and industrial Bacillus strains.

5. The method of claim 1, wherein the cell of Bacillus is selected from the group consisting of *Bacillus subtilis, Bacillus licheniformis, Bacillus lentus, Bacillus brevis,*

*Bacillus stearothermophilus, Bacillus alkalophilus, Bacillus amyloliquefaciens, Bacillus coagulans, Bacillus circulans, Bacillus lautus, Bacillus megaterium,* and *Bacillus thuringiensis.*

6. The method of claim 1, wherein the DNA construct is integrated into the genome of the Bacillus cell.

7. The method of claim 1, in which the translocated polypeptide is a secreted polypeptide or a polypeptide of the secretory pathway of a secreting cell.

8. The method of claim 7, in which the polypeptide of the secretory pathway is an enzyme and the secretory polypeptide is PrsA.

9. The method of claim 7 further comprising recovering the secreted polypeptide.

10. A method of introducing a DNA construct encoding a polypeptide of interest into a cell of a Bacillus sp., comprising mixing (a) a population of bacterial donor cells harboring i) a plasmid comprising a DNA construct encoding a polypeptide of interest and at least one cis-acting DNA sequence required for the transfer of said plasmid by conjugation in the presence of a trans-acting mobilizing element, and ii) at least one DNA sequence encoding said trans-acting mobilizing element, and (b) a population of Bacillus sp. recipient cells, under conditions allowing the plasmid to be transferred from the population of donor cells to population of recipient cells by conjugation, the Bacillus sp. being an alkalophilic Bacillus sp., an industrial Bacillus strain and/or a mutant Bacillus strain having been mutated to be capable of producing and secreting the polypeptide of interest in an increased yield as compared to the corresponding unmutated strain.

11. A method of constructing a cell of a Bacillus sp. harboring a DNA construct encoding a polypeptide of interest, comprising mixing (a) a population of auxotrophic bacterial donor cells harboring i) a plasmid comprising a DNA construct encoding a polypeptide of interest and at least one cis-acting DNA sequence required for transfer of said plasmid by conjugation in the presence of a trans-acting mobilizing element, and ii) at least one DNA sequence encoding said trans-acting mobilizing element, and (b) a population of unmarked Bacillus sp. recipient cells, under conditions allowing the plasmid to be transferred from the population of auxotrophic donor cells to the population of unmarked recipient cells by conjugation, and the auxotrophic property of the donor cell is exploited to select for recipient cells.

12. A method of introducing a DNA construct encoding a polypeptide of interest into a cell of a Bacillus sp., comprising mixing (a) a population of bacterial donor cells harboring i) a curable plasmid comprising a DNA construct encoding a polypeptide of interest and at least one cis-acting DNA sequence required for transfer of said plasmid by conjugation in the presence of a trans-acting mobilizing element, and ii) at least one DNA sequence encoding said trans-acting mobilizing element, and (b) a population of Bacillus sp. recipient cells, under conditions allowing the plasmid to be transferred from the population of donor cells to the population of recipient cells by conjugation.

13. The method of claim 12, wherein the curable plasmid comprises a DNA sequence conferring temperature sensitivity to the plasmid.

* * * * *

UNITED STATES PATENT AND TRADEMARK OFFICE
CERTIFICATE OF CORRECTION

PATENT NO. : 5,843,720
DATED : December 1, 1998
INVENTOR(S) : Tangney et al.

It is certified that error appears in the above-identified patent and that said Letters Patent is hereby corrected as shown below:

Col. 12, line 17: delete "Mob$^+$Kin'" and insert --Mob$^+$Km$^r$--

Signed and Sealed this

Twenty-eighth Day of December, 1999

Attest:

Q. TODD DICKINSON

*Attesting Officer*     Acting Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCCACTGGAT CCAATTTTCG TTTGTTG      27

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCAAATTGAT CCAAGAGAAC CAAC      24

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CAACAAACGA AAATTGGATC CAGTGGG      27

-continued ( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCACATCATC ATCATAAGC        19

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CCGGCGGATC CAAGGGGTGA TCG        23

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGGGTACTAG TAACCCGGGC CCGGCGTAGA GGATCCATAC ACAAA        45

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTCGGAGCTC ATTATTAATC TGTTCAGCAA TCGGGC        36

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GTCGGAGCTC TGCCTTTTAG TCCAGCTGAT TTCAC        35